(12) United States Patent
Itoi et al.

(10) Patent No.: US 8,455,902 B2
(45) Date of Patent: Jun. 4, 2013

(54) OPTICAL DEVICE AND METHOD FOR MANUFACTURING OPTICAL DEVICE, AND CAMERA MODULE AND ENDOSCOPE MODULE EQUIPPED WITH OPTICAL DEVICE

(75) Inventors: Kiyokazu Itoi, Kyoto (JP); Toshiyuki Fukuda, Kyoto (JP); Yoshiki Takayama, Shiga (JP); Tetsushi Nishio, Kyoto (JP); Tetsumasa Maruo, Osaka (JP)

(73) Assignee: Panasonic Corporation, Osaka (JP)

( * ) Notice: Subject to any disclaimer, the term of this patent is extended or adjusted under 35 U.S.C. 154(b) by 172 days.

(21) Appl. No.: 13/193,075

(22) Filed: Jul. 28, 2011

(65) Prior Publication Data

US 2011/0285003 A1  Nov. 24, 2011

Related U.S. Application Data

(62) Division of application No. 11/968,763, filed on Jan. 3, 2008, now Pat. No. 8,013,350.

(30) Foreign Application Priority Data

Feb. 5, 2007  (JP) .................................. 2007-024945
Oct. 18, 2007  (JP) .................................. 2007-270759

(51) Int. Cl.
*H01L 31/0203* (2006.01)

(52) U.S. Cl.
USPC ............... 257/98; 257/99; 257/432; 257/433; 257/434; 257/E33.071; 257/E31.127

(58) Field of Classification Search
USPC .............. 257/98, 99, 432, 433, 434, E33.071, 257/E31.127
See application file for complete search history.

(56) References Cited

U.S. PATENT DOCUMENTS

| 7,180,149 B2 * | 2/2007 | Yamamoto et al. ........... 257/434 |
| 7,616,250 B2 | 11/2009 | Watanabe et al. .............. 348/340 |
| 2004/0130640 A1 | 7/2004 | Fujimori ........................ 348/294 |
| 2005/0056903 A1 | 3/2005 | Yamamoto et al. ........... 257/433 |
| 2005/0275741 A1 | 12/2005 | Watanabe et al. |
| 2006/0023108 A1 | 2/2006 | Watanabe et al. .............. 348/335 |
| 2006/0043514 A1 | 3/2006 | Shizuno |
| 2008/0042227 A1 | 2/2008 | Asano et al. |
| 2009/0046183 A1 | 2/2009 | Nishida et al. |
| 2009/0085134 A1 | 4/2009 | Park et al. |

FOREIGN PATENT DOCUMENTS

| CN | 1728396 A | 2/2006 |
| JP | 1-276772 | 11/1989 |
| JP | 4-23469 | 1/1992 |
| JP | 2002-335020 | 11/2002 |

(Continued)

*Primary Examiner* — Minh-Loan T Tran
(74) *Attorney, Agent, or Firm* — Panasonic Patent Center

(57) ABSTRACT

An optical device is equipped with a light receiving region 16a and a peripheral circuit region 22 located around the light receiving region 16a on a major surface of an light receiving element 11a; electrodes for external connection 15 electrically connected to the peripheral circuit region 22 formed on a back surface opposite to the major surface of the light receiving element 11a; a transparent member 12 covering the light receiving region 16a adhered on the major surface of the light receiving element 11a with a light-transmitting adhesive 13; and a molding resin 14 for coating side surfaces of the transparent member 12 and the major surface of the light receiving element 11a excluding the region covered with the transparent member 12.

18 Claims, 13 Drawing Sheets

FOREIGN PATENT DOCUMENTS

| | | |
|---|---|---|
| JP | 2003-31782 | 1/2003 |
| JP | 2003-332542 | 11/2003 |
| JP | 2004-165191 A | 6/2004 |
| JP | 2006-5029 | 1/2006 |
| JP | 2006-303481 A | 11/2006 |
| JP | 2009-088459 A | 4/2009 |
| WO | 2006/073085 | 7/2006 |

* cited by examiner

OPTICAL DEVICE AND METHOD FOR MANUFACTURING OPTICAL DEVICE, AND CAMERA MODULE AND ENDOSCOPE MODULE EQUIPPED WITH OPTICAL DEVICE

FIELD OF THE INVENTION

The present invention relates to an optical device used in a solid-state image device, a photo IC, a light receiving device such as a photo coupler, and a small endoscope module, for disaster, for investigating buried cultural properties and for medical treatments, equipped with a light emitting device, such as an LED and a surface-emitting laser; a method for manufacturing such an optical device; and a camera module and an endoscope module equipped with such an optical device.

BACKGROUND OF THE INVENTION

In resent years, in portable electronic devices and the like, the reduction in the size, thickness and weight of electronic devices, and the high-density mounting of semiconductor devices have been strongly demanded. Furthermore, with the high integration of semiconductor elements caused by the progress of micro-fabrication technology, a technology known as a chip-mounting technology wherein semiconductor elements, such as chip-size packages and bear chips are directly mounted has been proposed. Such trends are also seen in optical devices, and various configurations have been disclosed.

For example, as in a sectional view of a conventional solid-state image device shown in FIG. 16, an element structure and a method for manufacturing such an element structure for realizing the reduction in the thickness and manufacturing costs of a solid-state image device 100 by directly adhering a transparent member 102 using a low-refractive-index adhesive 103 onto micro lenses 104 in an imaging region 105 of a solid-state image element 101 in the solid-state image device 100 have been disclosed.

The method is a method wherein the micro lenses 104 are directly formed on the solid-state image element 101 having the imaging region 105, and the transparent member 102 is directly adhered on the micro lenses 104 maintaining parallelism to the imaging region 105. At this time, by filling the low-refractive-index adhesive 103 between the micro lenses 104 and the transparent member 102 without a gap therebetween, electrical properties and optical properties are secured, and reliability is also secured, even if there is change in environmental conditions for using the solid-state image device 100. In the solid-state image device 100, the transparent member 102 is directly adhered on the micro lenses 104 on the solid-state image element 101 to protect the solid-state image element 101. Therefore, no air region wherein neither resin nor the like is filled between the micro lenses 104 and the transparent member 102, which is a part of the package, is present, and a region from the bottom surface of the solid-state image element 101 to the transparent member 102 can be mounted on the circuit module and the like as the thickness of the solid-state image device 100. As described above, since the solid-state image device 100 can be directly mounted in the circuit module and the like without using a ceramic package equipped with a glass lid, the thin solid-state image device 100 has been realized at low manufacturing costs.

A method for manufacturing another conventional solid-state image device of another configuration will be described referring to FIG. 17.

FIG. 17 is a step sectional view showing a conventional method for manufacturing a solid-state image device.

First, a plurality of solid-state image elements 111 are aligned and adhered on a surface of a substrate 110 with imaging regions thereof facing up at specified intervals as shown in FIG. 17A; the imaging region of each of the solid-state image elements 111 is coated with a flexible protective film 112 individually formed as shown in FIG. 17B; and the solid-state image elements 111 coated with the protective films 112 are compressed by a mold having flat compressing surfaces together with the substrate 110, and gaps surrounded by the compressing surfaces of the mold, the protective films 112 and the adjacent solid-state image elements 111 are filled with a molding resin 113 for resin molding as shown in FIGS. 17C and 17D. Then, the protective films 112 are removed from the imaging regions of the solid-state image elements 111 as shown in FIG. 17E; a transparent member 114 is adhered on the entire surface of the substrate 110 so as to coat the imaging region of each of the solid-state image elements 111 via the molded molding resin 113 as shown in FIG. 17F; and the solid-state image elements 111 are cut along the boundaries with the adjacent solid-state image elements 111 to form isolated solid-state image devices 115 as shown in FIG. 17G to realize cost reduction.

However, in the solid-state image device shown in FIG. 16, since a peripheral circuit region 107 including electrode pads 106 on the solid-state image elements 101 is not protected, the peripheral circuit region 107 must be individually molded with, for example, a liquid resin after being mounted on the circuit substrate using wire bonding or the like, and cost reduction is difficult.

Furthermore, when the transparent member 102 is directly adhered on the micro lenses 104 on the solid-state image element 101 with the adhesive 103, the adhesive 103 disadvantageously flows into the electrode pads 106 of terminal electrodes outside the imaging region 105 on the solid-state image element 101 to coat the electrode pads 106, resulting in the difficulty of bonding.

There was also a case in which moisture disadvantageously enters from the adhered boundary between the solid-state image element 101 and the transparent member 102, lowering moisture resistance.

In the solid-state image device shown in FIG. 17, although peripheral circuit regions including electrode pads and bonding wires of the solid-state image element 111 are collectively molded by transfer molding with the molding resin 113, since the protective film 112 is directly adhered on the imaging region of the solid-state image element 111 before molding and the protective film 112 is removed after molding, a gap 116 is left between the solid-state image element 111 and the transparent member 114 after removing the protective film 112 resulting in the difficulty of the thickness reduction of the solid-state image device 115.

Since the gap 116 is formed on the imaging region of the solid-state image element 111 as shown in FIG. 17G after removing the protective film 112, the strength of the solid-state image element 111 is disadvantageously lowered.

If the resin of the protective film 112 remains between micro lenses of the solid-state image element 111 when the protective film 112 is removed, it is difficult to discharge the remaining resin from the gap 116, leading to the lowering of long-term reliability.

Furthermore, molding must be carried out so that the bonding wires are buried in the molding resin 113, resulting in the difficulty of thickness reduction.

To solve the above problems, an object of the present invention is to provide a small, thin and high-quality optical device that excels in moisture resistance and prevents deterioration of strength, and a method for manufacturing such an optical device; and a camera module and an endoscope module equipped with such an optical device.

DISCLOSURE OF THE INVENTION

To solve the conventional disadvantages, an optical device according to the present invention is equipped with one of a light receiving region and a light emitting region, and a peripheral circuit region located around one of the light receiving region and the light emitting region formed on a major surface of an optical element; electrodes for external connection electrically connected to the peripheral circuit region formed on a back surface opposite to the major surface of the optical element; a light-transmitting member covering one of the light receiving region and the light emitting region adhered on the major surface of the optical element with a light-transmitting adhesive; and a molding resin for coating side surfaces of the light-transmitting member and the major surface of the optical element excluding the region covered with the light-transmitting member.

A step is formed on the side surfaces of the transparent member.

Alternatively, the side surfaces of the transparent member are slanted.

The upper surface of the molding resin is as high as or higher than the upper surface of the transparent member.

The optical element is one of a solid-state image element, a photo IC, an LED, and a laser.

A camera module according to the present invention is equipped with an optical device wherein the optical element is one of a solid-state image element, and a photo IC.

An endoscope module according to the present invention is equipped with the above-described optical device.

A method for manufacturing an optical device of the present invention has the steps of preparing an optical element wafer wherein a plurality of optical elements are vertically and horizontally arranged each having one of a light receiving region and a light emitting region, and a peripheral circuit region located around one of the light receiving region and the light emitting region on a major surface, and electrodes for external connection electrically connected to the peripheral circuit region formed on a back surface opposite to the major surface of the optical element; adhering a light-transmitting member on one of each light receiving region and light emitting region in the optical element wafer using a light-transmitting adhesive; coating side surfaces of the light-transmitting member and the major surface of the optical element wafer with a molding resin while allowing release sheets to intervene between a mold surface and the upper and lower surfaces of the optical element wafer, and clamping the system to fabricate an optical device wafer; and for dividing the optical device wafer removed out of the mold into individual devices.

Another method for manufacturing an optical device has the steps of preparing an optical element wafer wherein a plurality of optical elements are vertically and horizontally arranged each having one of a light receiving region and a light emitting region, and a peripheral circuit region located around one of the light receiving region and the light emitting region on a major surface, and electrodes for external connection electrically connected to the peripheral circuit region formed on a back surface opposite to the major surface of the optical element; adhering a light-transmitting member on one of each light receiving region and light emitting region in the optical element wafer using a light-transmitting adhesive; coating side surfaces of the light-transmitting member and the major surface of the optical element wafer with a molding resin by applying a liquid molding resin using screen printing to fabricate an optical device wafer; and dividing the optical device wafer into individual devices.

The method for manufacturing an optical device wherein a surface protecting seal is adhered on a major surface of the light-transmitting member opposite to the optical element; has also a step of removing the surface protecting seal after the step of coating the side surfaces of the light-transmitting member and the major surface of the optical element wafer with the molding resin to fabricate the optical device wafer.

DESCRIPTION OF THE EMBODIMENTS

Figure 1:
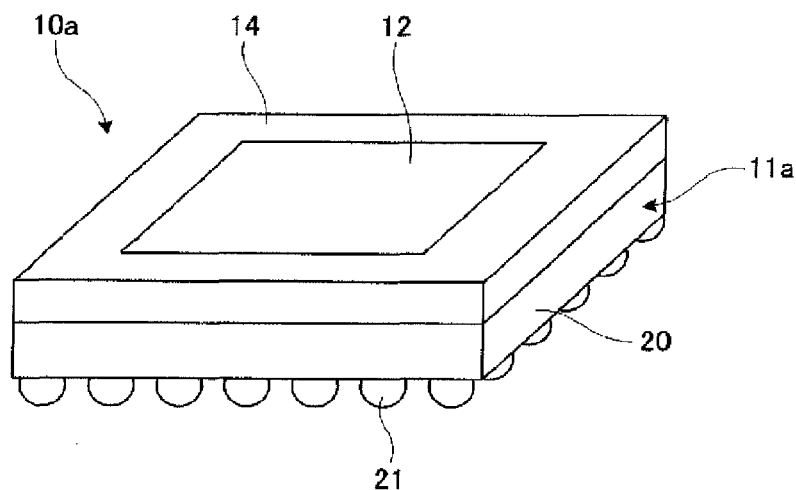
FIG. 1 is a schematic perspective view showing an optical device according to a first embodiment of the present invention.

The embodiments of the present invention will be described referring to the drawings. In the drawings, the thickness, length and the like of each part are different from actual ones for convenience of preparation of the drawings. The number of electrodes on an optical element and the number of electrodes for external connection are also different from actual ones for ease of illustration. Furthermore, the materials for each constituting member are not limited to the materials in the following descriptions.

First Embodiment

First, the first embodiment will be described referring to FIGS. 1 to 5.

Figure 2A:
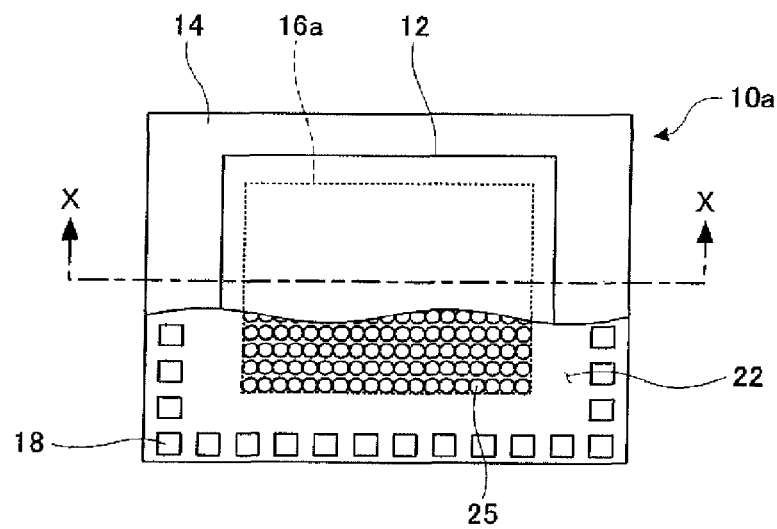
FIG. 2A is a plan view showing the optical device according to the first embodiment viewed from a transparent member side.
Figure 2B:
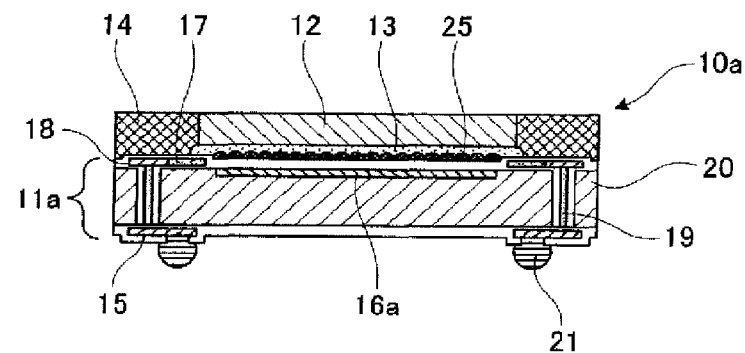
FIG. 2B is a sectional view showing the optical device according to the first embodiment.

FIG. 1 is a schematic perspective view showing an optical device according to the first embodiment of the present invention. FIGS. 2A and 2B are diagrams showing the configuration of the optic device; FIG. 2A is a plan view showing the optical device according to the first embodiment viewed from a transparent member side; and FIG. 2B is a sectional view showing the optical device according to the first embodiment, which is the sectional view taken along the line X-X in FIG. 2A. To make the drawing clearly understandable, FIG. 2A shows a state in which part of a transparent member and molding resin have been removed. Here, as an example of the optical device, a solid-state image device is used, and the configuration of a solid-state image device 10a (an example of optical devices) will be described referring to FIGS. 1 and 2.

As shown in FIGS. 1 and 2, the solid-state image device 10a is equipped with a solid-state image element 11a, which is an example of optical elements; a light transmitting member, such as a transparent member 12; and a molding resin 14.

On a major surface of the solid-state image element 11a, an imaging region 16a (an example of light receiving regions) formed in the vicinity of the center, and a peripheral circuit region 22 located around the imaging region 16a are provided. In the imaging region 16a, micro lenses 25 are formed on each pixel arrayed.

The peripheral circuit region 22 has a plurality of element electrodes 18 to connect peripheral circuits with an internal wiring 17, and the internal wiring 17 is electrically connected to the element electrodes 18. A plurality of electrodes for external connection 15 are provided on a back surface opposite to the major surface of the solid-state image element 11a. The electrodes for external connection 15 are electrically connected to the element electrodes 18 via penetration electrodes 19 formed on a semiconductor substrate 20. Although embodiments using silicon as the material of the semiconductor substrate 20 are described here, one of group III-V compounds and group II-VI compounds may also be used in consideration of application to semiconductor laser and light emitting diode.

The transparent member 12 is adhered onto the major surface of the solid-state image element 11a using a light transmitting adhesive, such as a light-transmitting adhesive 13, and is disposed so as to coat the entire surface of the imaging region 16a. Upper and lower surfaces of the transparent member 12 are parallel to each other and are processed to be optical flat surfaces. Side surfaces of the transparent member 12 are perpendicular to the upper and lower surfaces, and have rectangular project planes. In the project planes of the transparent member 12, four corners may be cut at an angle of about 45°, and each edge of one of or both of the upper and lower surfaces may be chamfered.

The material of the transparent member 12 may be, for example, a borosilicate glass plate, and may be a low-pass filter consisting of one of a quartz plate and a calcite plate having birefringence properties to prevent moiré due to fringes in specific directions. Alternatively, a low-pass filter wherein quartz plates or calcite plates are adhered on both sides of an infrared cut filter so that birefringence properties intersect at right angles to one another, may be used. Furthermore, one of a transparent epoxy resin plate, an acrylic resin plate, and a transparent alumina plate can also be used. The thickness of the transparent member 12 when the borosilicate glass plate is used is within a range of 200 μm to 1000 μm, preferably within a range of 300 μm to 700 μm. The reason why the minimum thickness is 200 μm is to realize the size and thickness reduction so that, when the solid-state image device 10a composed of the transparent member 12, the light-transmitting adhesive 13, the molding resin 14, the solid-state image element 11a, and the electrodes for external connection 15 is mounted, the height is not more than 500 μm; and the reason why the maximum thickness is 1000 μm is to realize a transmittance of at least 90% to incident light of a wavelength of 500 nm. The reason why the preferable thickness range is from 300 μm to 700 μm is that the thickness range makes it possible to produce the solid-state image device 10a most stably using the present manufacturing technique, and a small and thin solid-state image device 10a can be realized at low manufacturing costs by applying inexpensive general-purpose materials to the components. When one of alumina and a transparent resin is used in the transparent member 12, the thickness of each transparent member 12 must be determined taking the difference in transmittance into consideration; and in the case of quartz and calcite, since the distance of double image due to birefringence relates to the thickness of the transparent member 12, the thickness must be determined taking into consideration the distance between pixels of the solid-state image element 11a in addition to the difference in transmittance.

The light-transmitting adhesive 13 is an optical light-transmitting adhesive used when the transparent member 12 is adhered on the imaging region 16a, and may be, for example, an acrylic resin, an epoxy resin with resin composition having no absorption edge within the wavelength range of visible light, or a polyimide resin. The light-transmitting adhesive 13 has cured properties of lower refractive index than the micro lenses 25 formed on the imaging region 16a, and the cured properties can be performed by one of or both of ultraviolet irradiation and heating.

The molding resin 14 coats the side surfaces of the transparent member 12, and the major surface (upper surface) of the solid-state image element 11a excluding the region coated with the transparent member 12. The molding resin 14 is a light shielding resin having a flat upper surface and a thickness being substantially the same as the transparent member 12. Although embodiments using an epoxy resin as the material for the molding resin 14 are described here, biphenyl resins or silicone resins may also be used when a low-elasticity cured article is applied for reducing the thickness of the semiconductor substrate 20 or for improving the thermal impact resistance or moisture resistance of the solid-state image device 10a.

When a layer of the molding resin 14 is formed by transfer molding using a mold, the molding resin 14 is composed of an epoxy resin, which is a major component, in a state in which semi-cured powder resin is in a tablet form; a curing agent; a curing promoting agent, powdered silica as an inorganic filler; a flame retardant; carbon black as a pigment; and a mold release. When the layer of the molding resin 14 is formed by screen printing, a liquid molding resin 14 composed of the above-described compounding components excluding the mold release is used.

Especially, the selection and compounding quantity of the inorganic filler and pigment in the molding resin 14 used in the solid-state image device 10a of the present embodiment are important for the warpage and light shielding of the solid-state image device 10a. Therefore, it is necessary to suppress the warpage of the solid-state image device 10a by compounding as much of the inorganic filler as possible insofar as the flow (viscosity) of the molten resin during molding is not affected to make the linear expansion coefficient approach the linear expansion coefficient of the solid-state image element 11a and the transparent member 12. Further, to prevent the breakdown of wirings due to the corrosion of the wirings of the solid-state image element 11a by lowering the moisture absorption of the cured article, high-purity silica produced by melting to remove crystallinity therefrom is processed in spheres of various diameters and is properly compounded.

Furthermore, by compounding as much the pigment as possible in the cured article of the molding resin 14 insofar as the electrical resistance of the cured article of the resin is not lowered in a high-temperature and high-humidity environment to induce the defective insulation of the solid-state image device 10a, the incident light around the transparent member 12 is prevented from entering from the side surfaces of the transparent member 12 to become stray light. As the pigment, for example, carbon black of a tone having high light-shielding properties is used to prevent a part of the incident light from the above the molding resin 14 from reaching the p-n junction and the gate portions of the passive element and active element on the major surface of the solid-state image element 11a so as to avoid the malfunction of the solid-state image element 11a. It is also important to select the material having a particle diameter that can increase the compounding quantity and having a low polarizing property.

Conductive electrodes 21 for mounting on the circuit substrate of electronic device are formed on the electrodes for external connection 15. The conductive electrodes 21 may be, for example, solder balls, or a resin ball with a conductive film formed on the surface or may be bumps (stud bumps) formed by wire bonding. In the case of solder balls, solder materials having various compositions, such as Sn—Ag—Cu, Sn—Ag—Bi, and Zn—Bi, can be used. Although the conductive electrodes 21 can be mounted on the circuit substrate by soldering when solder balls are used for the conductive electrodes 21, an electrically conductive adhesive can also be used for mounting. When the conductive resin ball is used, either soldering or adhesion by the electrically conductive adhesive can be used. Alternatively, the conductive electrodes 21 can be formed by supplying a solder paste onto the electrodes for external connection 15 using, for example, screen printing, and reflowing.

As described above, by coating at least the imaging region 16a with the transparent member 12, and molding with the molding resin 14 the side surfaces of the transparent member 12 and the surface of the peripheral circuit region 22 not coated with the transparent member 12, since the imaging region 16a can be protected by the transparent member 12 and the peripheral circuit region 22 can be protected by the molding resin 14, the mechanical damage on the major surface of the solid-state image device 10a can be prevented. Furthermore, since the entire major surface of the solid-state image element 11a is coated with the molding resin 14 and the light-transmitting adhesive 13, the strength of the solid-state image element 11a can be prevented from lowering.

Furthermore, since the invasion of moisture from the adhered boundary between the transparent member 12 and the solid-state image element 11a can be prevented by the molding resin 14, the solid-state image device 10a having excellent moisture resistance and high reliability can be fabricated.

Also by forming the molding resin 14 on the side surfaces of the transparent member 12, flare, smear, or the like caused by stray light generated by the invasion of external reflected light from the side surfaces of the transparent member 12 can be prevented. Furthermore, since the solid-state image device 10a requires no housing, and the transparent member 12 is directly adhered on the major surface of the solid-state image element 11a with the light-transmitting adhesive 13, the reduction of the size and thickness of the chip can be realized.

Figure 3A:
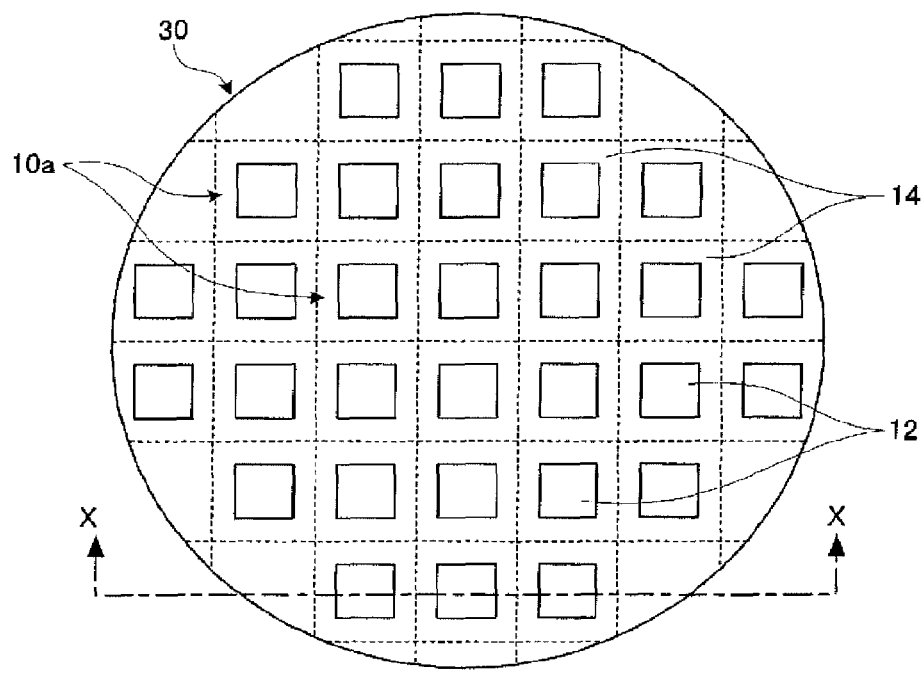
FIG. 3A is a plan view showing the configuration of the optical device wafer according to the first embodiment.
Figure 3B:
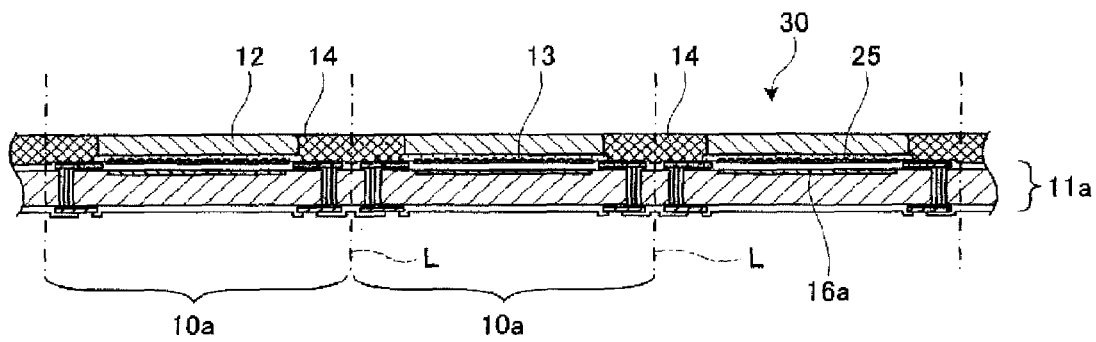
FIG. 3B is a sectional view showing the configuration of the optical device wafer according to the first embodiment.

Next, the configuration of a solid-state image device wafer 30 will be described referring to FIGS. 3A and 3B. FIGS. 3A and 3B are diagrams of the solid-state image device wafer 30 wherein a plurality of solid-state image devices 10a are arrayed vertically and horizontally; FIG. 3A is a plan view showing the configuration of the optical device wafer according to the first embodiment; and FIG. 3B is a sectional view taken along the line X-X in FIG. 3A showing the configuration of the optical device wafer according to the first embodiment. The solid-state image device wafer 30 is an embodiment of the optical device wafer, and a solid-state image device wafer will be described as an example.

The solid-state image device wafer 30 is composed of a plurality of the solid-state image elements 11a arranged vertically and horizontally at even intervals; the transparent members 12 disposed on the micro lenses 25 formed in the imaging region 16a of each solid-state image element 11a; the light-transmitting adhesive 13 for adhering the solid-state image elements 11a to the transparent members 12; and the molding resin 14 for forming a light-shielding layer between the adjoining transparent members 12 on the major surface of the wafer.

The solid-state image device wafer 30 may be resin molded without adhering the transparent member 12 on the imaging region 16a of the solid-state image element 11a rejected in the electrical test or the optical test; alternatively, resin molding may be carried out after adhering an inexpensive dummy block having the same size as the transparent member 12 for maintaining the flatness of the upper surface of the molding resin 14 during resin molding. The dummy block is formed of a material, such as resins and silicones.

Since the solid-state image device wafer 30 can be fabricated in a wafer form without wasting the expensive transparent members 12 by adhering the transparent members 12 only on the imaging regions 16a of the solid-state image elements 11a accepted in the test, or by adhering the dummy blocks on the locations of the solid-state image elements 11a rejected in the test as described above, a thin solid-state image device wafer 30 can be realized at low costs.

Figure 4A:
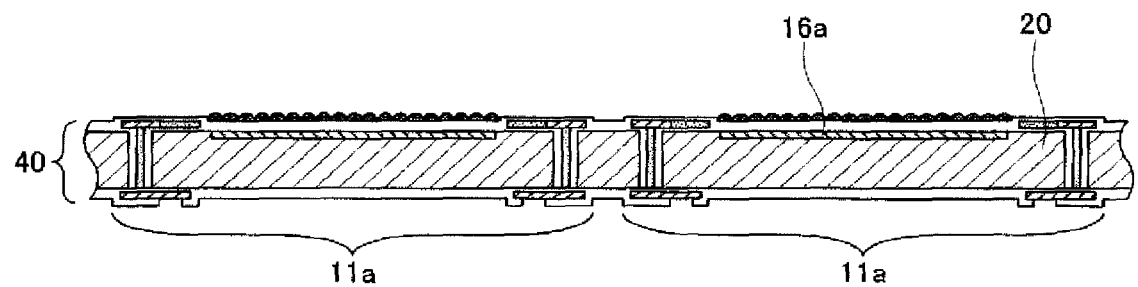
FIG. 4A is a step sectional view showing the step of preparing a solid-state image element wafer in a method for manufacturing the optical device according to the first embodiment.
Figure 4B:
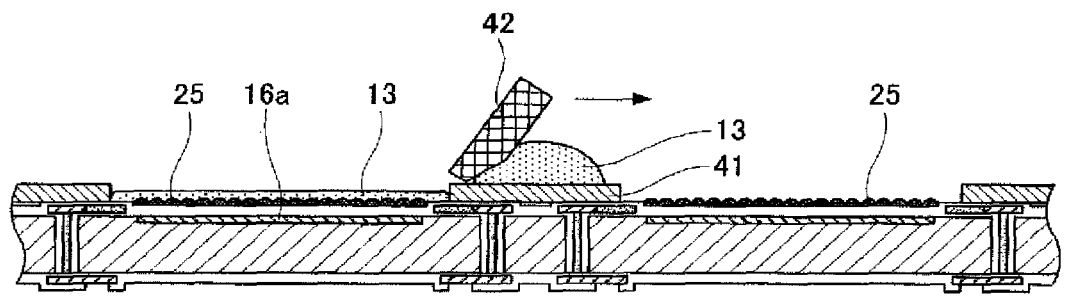
FIG. 4B is a step sectional view showing the step of applying a light-transmitting adhesive in the method for manufacturing the optical device according to the first embodiment.
Figure 4C:
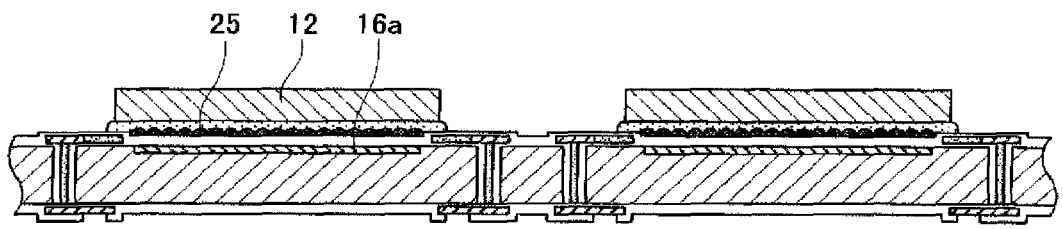
FIG. 4C is a step sectional view showing the step of adhering a transparent member in the method for manufacturing the optical device according to the first embodiment.
Figure 5A:
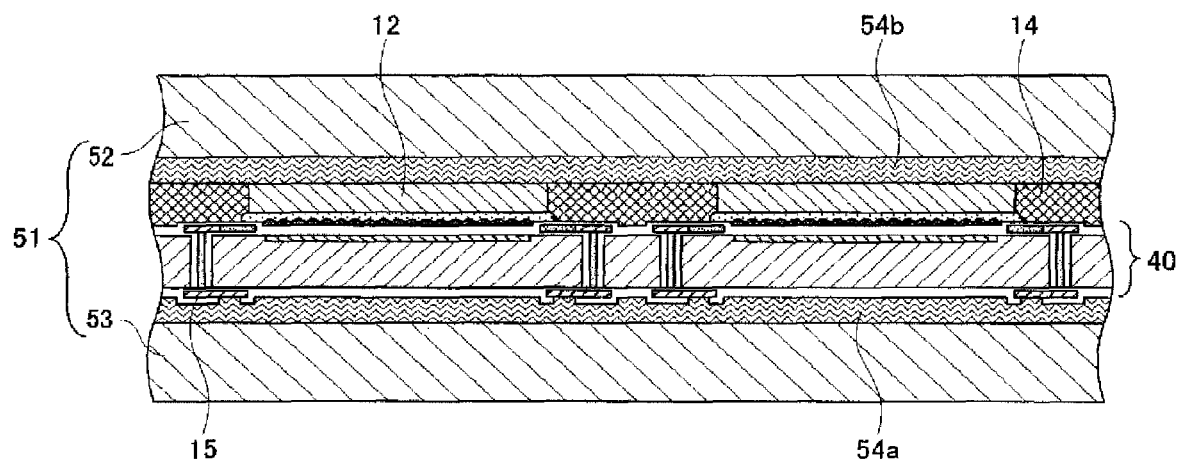
FIG. 5A is a step sectional view showing the resin molding step in the method for manufacturing the optical device according to the first embodiment.
Figure 5B:
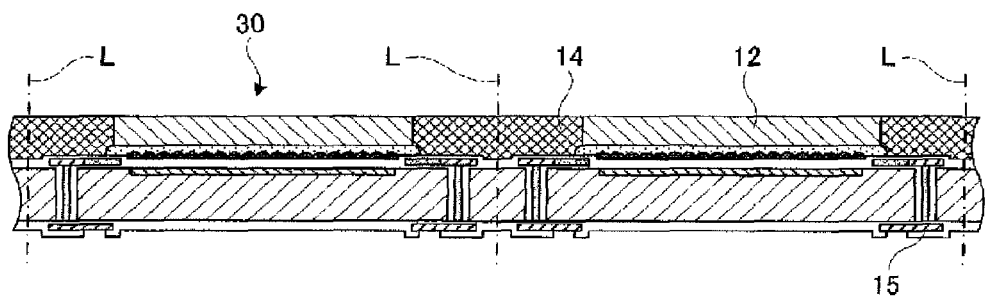
FIG. 5B is a step sectional view showing the configuration of the optical device wafer manufactured by the method for manufacturing the optical device according to the first embodiment.
Figure 5C:
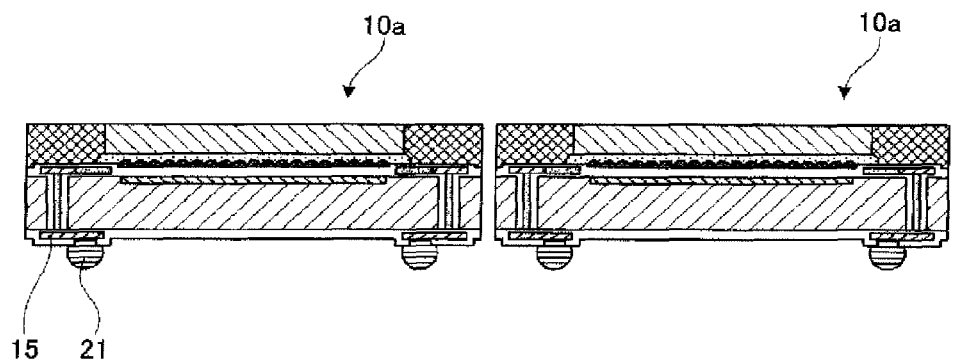
FIG. 5C is a step sectional view showing the dividing step in the method for manufacturing the optical device according to the first embodiment.

Next, a method for manufacturing the solid-state image device 10a will be described referring to FIGS. 4 and 5. FIG. 4A is a step sectional view showing the step of preparing a solid-state image element wafer in a method for manufacturing the optical device according to the first embodiment; FIG. 4B is a step sectional view showing the step of applying the light-transmitting adhesive in the method for manufacturing the optical device according to the first embodiment; and FIG. 4C is a step sectional view showing the step of adhering the transparent member in the method for manufacturing the optical device according to the first embodiment. These are sectional views showing the steps from preparing the semiconductor substrate 20 on which the plurality of solid-state image elements 11a arranged vertically and horizontally at even intervals are formed, to adhering the transparent member 12 on the imaging region 16a of each solid-state image element 11a in the method for manufacturing the solid-state image device 10a. FIG. 5A is a step sectional view showing the resin molding step in the method for manufacturing the optical device according to the first embodiment; FIG. 5B is a step sectional view showing the configuration of the optical device wafer manufactured by the method for manufacturing the optical device according to the first embodiment; FIG. 5C is a step sectional view showing the dividing step in the method for manufacturing the optical device according to the first embodiment. These are sectional views showing the steps from molding with the molding resin 14 the region excluding the transparent member 12 on the major surface of the semiconductor substrate 20 to fabricate the solid-state image device wafer 30, to dividing the solid-state image device wafer 30 into a plurality of the solid-state image devices 10a to form conductive electrodes 21. Here, a solid-state image device is also used for the description as an example of optical devices.

First, as shown in FIG. 4A, a solid-state image element wafer 40 (an example of optical element wafers) including the semiconductor substrate 20 on which the plurality of solid-state image elements 11a are vertically and horizontally arrayed is prepared. Every solid-state image element 11a has been subjected to electrical and optical tests in the wafer state.

FIG. 4B shows the step of applying the light-transmitting adhesive 13. The light-transmitting adhesive 13 is applied onto the micro lenses 25 in the imaging region 16a situated in the central portion of each solid-state image element 11a by, for example, screen printing to form a coating film. At this time, the light-transmitting adhesive 13 supplied onto a mask 41 is flowed onto the imaging region 16a through the pattern of the mask 41 using a squeegee 42.

Although, for example, an ultraviolet setting liquid acrylic resin having a lower refraction index than the micro lenses is used for the light transmitting adhesive, such as the light-transmitting adhesive 13, the curing property may be heat setting, or may be both ultraviolet setting and heat setting properties. The material for the light-transmitting adhesive 13 may be one of an epoxy resin and an acrylic resin, or may be a polyimide resin. The method for forming the coating film of the light-transmitting adhesive 13 may be one of a drawing method, a potting method, and a stamping method; and a semi-cured prepreg sheet may also be used. Furthermore, the coating film of the light-transmitting adhesive 13 may be formed only on the location of the solid-state image elements 11a accepted in the test.

FIG. 4C is a sectional view showing the step of adhering the light transmitting member, such as the transparent member 12. In this step, the transparent member 12, such as borosilicate glass divided into pieces having a size to coat the entire surface of the imaging region 16a is placed on the imaging region 16a of each solid-state image element 11a to which the light-transmitting adhesive 13 has been applied of the solid-state image element wafer 40, so as not to introduce the air. At this time, the transparent member 12 may be placed on the light-transmitting adhesive 13 in a reduced-pressure atmosphere while defoaming. The transparent member 12 may be adhered to the micro lenses 25 in the imaging region 16a by aligning the transparent member 12 to the surface of the imaging region 16a in parallel at the proper location on the imaging region 16a, and radiating ultraviolet beams having predetermined optical energy, or by heating after ultraviolet irradiation. The transparent member 12 may be any of quartz, calcite, alumina, and transparent resins.

FIG. 5A is a sectional view showing the step of resin molding. In this step, the side surfaces of the transparent member 12 and the major surface of the solid-state image element 11a in the region excluding the transparent member 12 are coated with the epoxy molding resin 14 to form a layer of the molding resin 14 having the same thickness as the thickness of the transparent member 12 by transfer molding using a mold for resin molding 51. The material for the molding resin 14 may be biphenyl resins or silicone resins.

The mold for resin molding 51 is composed of an upper mold 52 and a flat lower mold 53, and is preheated to a temperature range of 160° C. to 210° C. at which the molding resin 14 is melted, preferably, a temperature range of 175° C. to 195° C. In the lower mold 53, a thin release sheet 54a made of tensioned tetrafluoroethylene resin is disposed. The upper mold 52 is equipped with a cavity (not shown) having a depth substantially the same as the total thickness of the transparent member 12 and the solid-state image element wafer 40. The upper mold 52 is constituted so as to accommodate the solid-state image element wafer 40 on the surface thereof, and a thin release sheet 54b made of tensioned tetrafluoroethylene resin is disposed in the upper mold 52.

In the procedure for resin molding, the solid-state image element wafer 40 on which the transparent member 12 is adhered is placed on the predetermined location in the lower mold 53 via the release sheet 54a. When the solid-state image element wafer 40 is completely accommodated in the cavity via the release sheet 54b, the upper mold 52 is closed until the upper surface of the transparent member 12 on the major surface side and the electrodes for external connection 15 on the back side are compressed to the release sheets 54a and 54b, respectively. Thereafter, the molten molding resin 14 is injected into the cavity, and the upper and lower molds 51 are held in the closed (clamped) state until the molding resin 14 is cured in the cavity.

Then, the upper and lower molds 51 are opened after a predetermined time, and the resin-molded solid-state image element wafer 40, i.e., the solid-state image device wafer 30 (an example of optical device wafers) is taken out as shown in FIG. 5B. The time of holding the solid-state image element wafer 40 in the mold for resin molding 51 is the time until the cross-linking reaction of the molding resin 14 is progressed to reach a strength so that resistance to deformation is obtained. As described above, when the upper mold 52 is closed, since the upper surface of the transparent member 12 and the electrodes for external connection 15 are compressed to the release sheets 54a and 54b, respectively, the upper surface of the transparent member 12 and the back surface of the solid-state image element wafer 40 do not contact the molding resin 14. Therefore, the occurrence of scratches on the upper surface of the transparent member 12 and burrs on the molding resin 14 can be prevented. The release sheets 54a and 54b may be formed of other flexible heat-resistant resin films having no reactive groups.

Next, as shown in FIG. 5C, the solid-state image device wafer 30 after the resin molding step is divided into individual solid-state image devices 10a by cutting along the dividing line L using a dicer. For dividing, stealth dicing using a laser may also be used.

Finally, the conductive electrodes 21 are joined on the electrodes for external connection 15 of each solid-state image device 10a. In this step, to join solder balls as an example of the conductive electrodes 21 to a land plane on the back surface of the solid-state image device 10a, by applying a flux onto the land plane, placing solder balls thereon, and passing the solid-state image device 10a through a reflowing furnace set to a predetermined temperature distribution to join the solder balls onto the land, the solid-state image device 10a can be realized.

Although the conductive electrodes 21 of solder balls are formed after dividing the solid-state image device wafer 30 into individual solid-state image devices 10a in the above-described manufacturing method, the conductive electrodes 21 may be formed before dividing the solid-state image device wafer 30, and thereafter, the solid-state image device wafer 30 may be divided into individual solid-state image devices 10a. The conductive electrodes 21 may be plated bumps wherein thin gold films are formed on copper or nickel bases, or may be stud bumps formed by gold-ball bonding.

As described above, a plurality of solid-state image devices 10a can be collectively formed by applying processing in the wafer state of the first embodiment, and the manufacturing method wherein integral resin molding in the wafer state is performed using the mold for resin molding 51. Furthermore, the reduction of facility investment by compacting the production line, and the reduction of the thickness of the solid-state image devices 10a can be realized. Since the solid-state image element wafer 40 can be fabricated in the wafer state without wasting the expensive transparent member 12 by adhering the transparent member 12 only to the solid-state image elements 11a accepted in the test, or by connecting dummy blocks to the locations of the solid-state image elements 11a rejected in the test, an inexpensive solid-state image device 10a can be realized.

In the first embodiment, as shown in FIGS. 2 and 5, although the upper surface of the transparent member 12 of the solid-state image device 10a is aligned with the upper surface of the molding resin 14 (same height), the upper surface of the transparent member 12 may be higher than the upper surface of the molding resin 14 by burying (impressing) the upper surface and the upper ends of the sides of the transparent member 12 in the release sheet 54b when the mold 51 is closed as shown in FIG. 5A. Thereby, utilizing the impression of the release sheet 54b, the effect of avoiding the adhesion of the thin burr of the resin once liquefied in the mold 51 for resin molding to the upper surface of the transparent member can be obtained.

Second Embodiment

Next, the second embodiment of the present invention will be described referring to FIGS. 6A, 6B and 6C. The second embodiment is a manufacturing method in which resin molding of a solid-state image device wafer 30 is performed using not the mold for resin molding in the first embodiment, but screen printing.

Figure 6A:
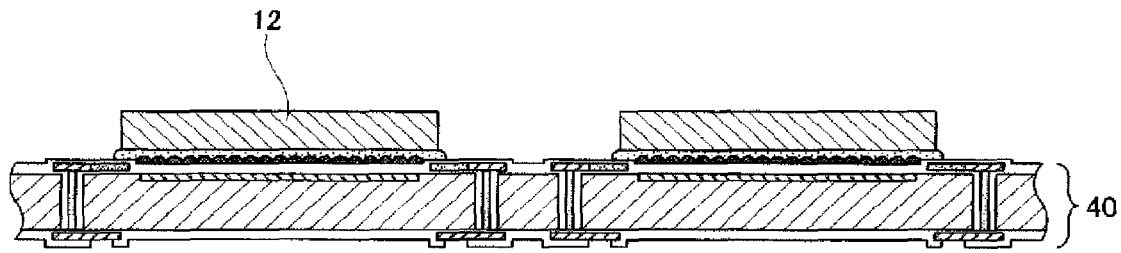
FIG. 6A is a step sectional view showing the step of adhering a transparent member in a method for manufacturing an optical device according to a second embodiment.

FIG. 6A is a step sectional view showing the step of adhering a transparent member in the method for manufacturing an optical device according to the second embodiment; and a solid-state image element wafer 40 is manufactured and prepared by the steps shown in the above-described FIG. 4. FIG. 6B is a step sectional view showing the resin molding step in the method for manufacturing the optical device according to the second embodiment; and FIG. 6C is a step sectional view showing the dividing step in the method for manufacturing the optical device according to the second embodiment.

Figure 6B:
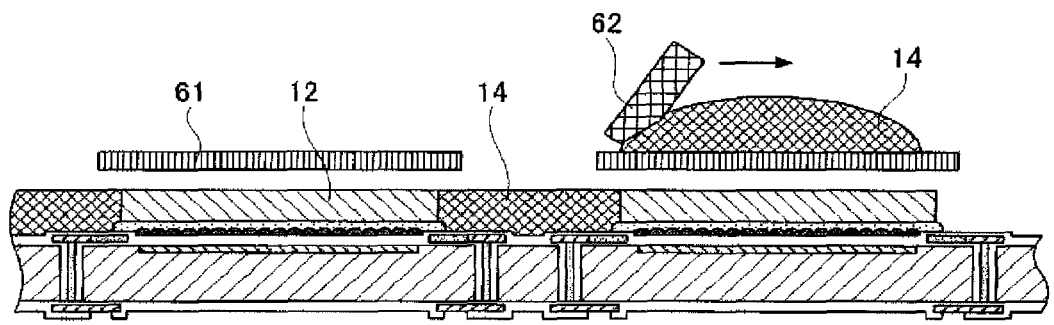
FIG. 6B is a step sectional view showing the resin molding step in the method for manufacturing the optical device according to the second embodiment.

In the resin molding step shown in FIG. 6B, side surfaces of a transparent member 12 and the major surface (upper surface) of the solid-state image element wafer 40 in the region excluding the transparent member 12 are coated with a liquid epoxy molding resin 14 by the screen printing using a screen printer to form a layer of the molding resin 14 having the same thickness as the transparent member 12 (i.e., flush with the upper surface of the transparent member 12). The material for the molding resin 14 may be a biphenyl resin or a silicone resin.

The screen printer is equipped with a metal mask for printing 61 wherein a pattern capable of applying the liquid molding resin 14 to the region excluding the transparent member 12 is formed. The sample table is preheated to a temperature in a range of 50° C. to 100° C., preferably of 65° C. to 85° C. at which the liquid molding resin 14 has a low viscosity. Then, a predetermined amount of the liquid molding resin 14 supplied onto the surface of the metal mask for printing 61 is poured from the pattern of the metal mask for printing 61 using a squeegee 62 and is applied to the region excluding the transparent member 12.

Thereafter, the solid-state image element wafer 40 may be kept horizontal in a clean environment until the liquid molding resin 14 is sufficiently spread. Alternatively, the solid-state image element wafer 40 may be kept horizontal in a reduced-pressure atmosphere while removing the air contained in the liquid molding resin 14.

Next, the solid-state image element wafer 40 is kept horizontal in a curing oven heated to a temperature in a range of 160° C. to 210° C., preferably of 175° C. to 195° C. for a predetermined time to cure the molding resin 14. Here, the molding resin 14 may be cured in two steps: preliminary curing and final curing. The molding resin 14 is heated until the cross-linking reaction is progressed and the strength to resist deformation is obtained.

Figure 6C:
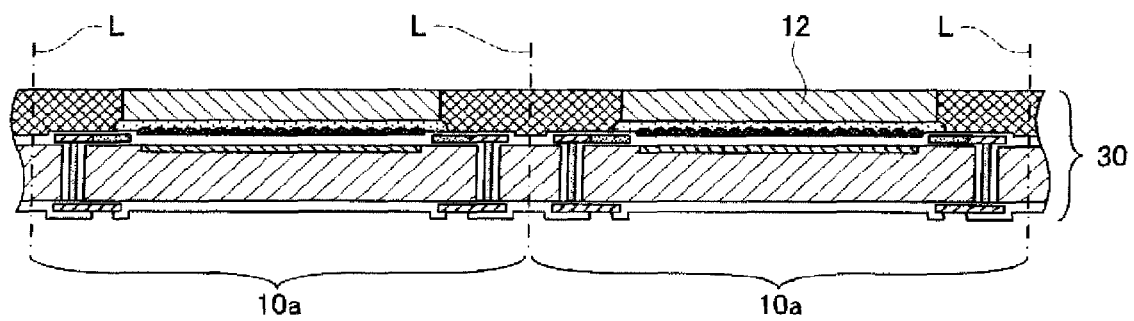
FIG. 6C is a step sectional view showing the dividing step in the method for manufacturing the optical device according to the second embodiment.

Thereafter, as shown in FIG. 6C, the solid-state image device wafer 30 after the above-described resin molding step is divided along the dividing line L into individual solid-state image devices 10a using a dicer, and the step of joining conductive electrodes 21 (refer to FIG. 5C) is performed to realize the solid-state image devices 10a.

As described above, by applying the processing in the wafer state and the manufacturing method wherein the integral resin molding is carried out using the molding resin 14, in addition to the advantages of moisture resistance and high strength obtained by the manufacturing method using the resin molding technique by transfer molding, and since a mold for resin molding 51 is not used, a mold release is not required in the composition of the molding resin 14. Thereby, the adhesion of the major surface of the solid-state image element wafer 40 and the side surfaces of the transparent member 12 to the molding resin 14 is reinforced, and the reliability of the solid-state image devices 10a is improved.

Third Embodiment

Figure 7:
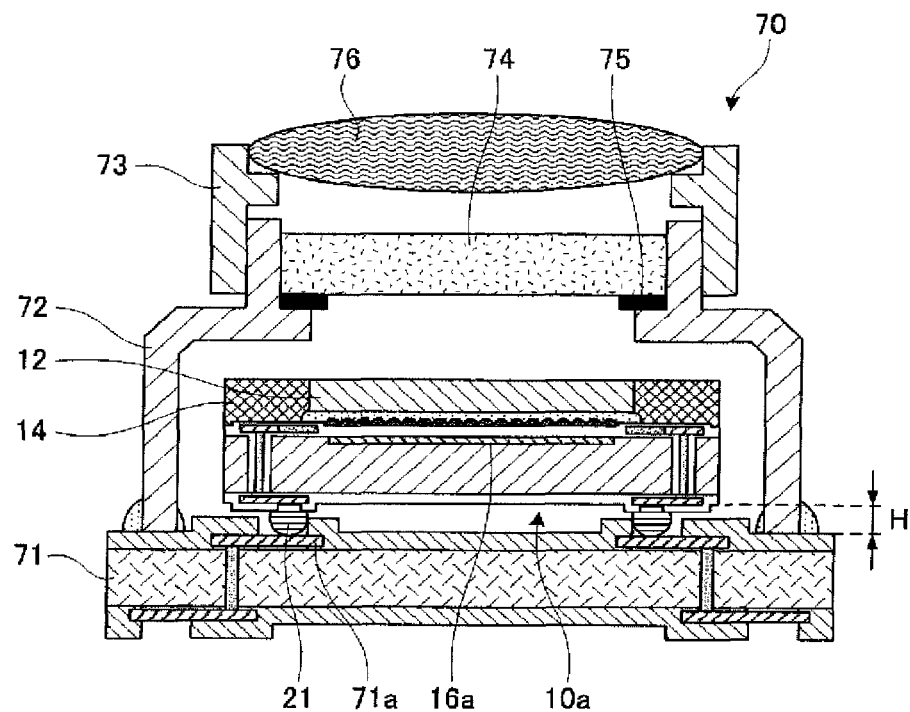
FIG. 7 is a sectional view showing a digital camera module according to a third embodiment.

Next, the third embodiment of the present invention will be described referring to FIG. 7. FIG. 7 is a sectional view showing a digital camera module according to the third embodiment; specifically, a sectional view showing a digital camera module 70, which is an application example of a solid-state image device 10a to electronic devices. The camera module 70 has a configuration wherein conductive electrodes 21 of the solid-state image device 10a are joined to a mounting lands 71a disposed on the central portion of the upper surface of a glass-epoxy wiring substrate 71, and the mounting height H of the solid-state image device 10a is within a range of about 0.5 mm to 0.7 mm. The wiring substrate 71 may also be a flexible wiring substrate composed of polyimide and the like.

Around the solid-state image device 10a, a fixed housing tube 72 having an opening wider than an imaging region 16a of the solid-state image device 10a is disposed and is adhered at a predetermined location on the upper surface of the wiring substrate 71. In the upper portion of the fixed housing tube 72, a sliding housing tube 73 equipped with a lens 76 is inserted, and after the focal point is adjusted, the sliding housing tube 73 is adhered to the fixed housing tube 72 using an adhesive (not shown). A configuration wherein a space is secured above the solid-state image device 10a in the fixed housing tube 72, and a low-pass filter 74 and a light shielding plate 75 are disposed in the space may also be used.

As described above, since the height from the upper end of the sliding housing tube 73 to the upper surface of the wiring substrate 71 can be lowered by designing the mounting height H of the thin solid-state image device 10a to be low, a thin digital camera can be realized. Furthermore, by securing a space above the solid-state image device 10a in the fixed housing tube 72, and disposing the low-pass filter 74 and the light shielding plate 75 in the space, a high-quality thin digital camera generating no moiré can be realized.

Fourth Embodiment

Figure 8:
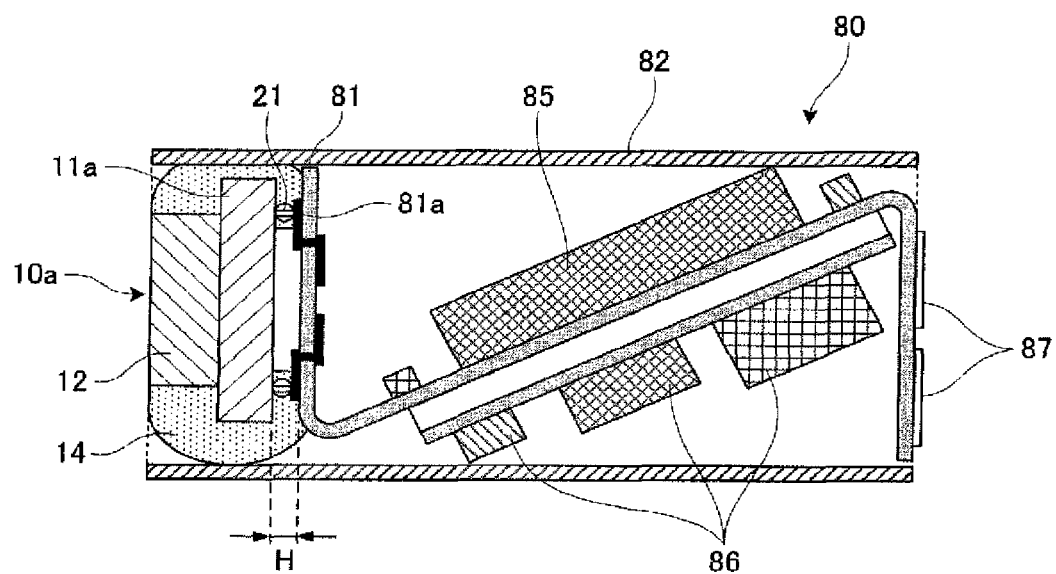
FIG. 8 is a sectional view showing an endoscope module according to a fourth embodiment.

Next, the fourth embodiment of the present invention will be described. FIG. 8 is a sectional view showing an endoscope module according to the fourth embodiment, and shows the cross section of an endoscope module 80 for disaster, for investigating buried cultural properties and for medical treatments as an application example of a solid-state image device 10a to electronic devices. The housing tube portion of the endoscope module 80 for disaster, for investigating buried cultural properties and for medical treatments has a configuration wherein conductive electrodes 21 of the solid-state image device 10a are joined to a flexible wiring substrate 81 and mounting lands 81a disposed on a surface close to the end portion of the flexible wiring substrate 81, and the mounting height H of the solid-state image device 10a is within a range of about 0.5 mm to 0.7 mm.

A semiconductor device for driving 85 and passive electronic parts 86 of peripheral circuits are joined to the joining side of the solid-state image device 10a close to the center portion of the flexible wiring substrate 81 and the mounting land on the opposite surface, respectively; and external electrodes 87 of the flexible wiring substrate 81 are formed on the surface opposite to the joining side of the solid-state image device 10a close to the other end portion of the flexible wiring substrate 81, which are electrically connected by wirings and through-holes on the flexible wiring substrate 81. The flexible wiring substrate 81 is bent at two locations so that the cross section has an inverted N-shape, and held in a housing tube 82. The center portion of the flexible wiring substrate 81 may have a configuration wherein back surfaces of a plurality of the flexible wiring substrates to which electronic parts are joined are laminated so as to form a circuit for imparting high added value functions to a surface of the other flexible wiring substrate.

By bending the flexible wiring substrate 81 wherein electrical parts for driving circuit and power circuit parts are mounted and holding the flexible wiring substrate 81 in a small housing tube together with the solid-state image device 10a, a small, thin, and high-quality endoscope module 80 for disaster, for investigating buried cultural properties and for medical treatments, excellent in moisture resistance and preventing deterioration of strength can be realized.

Fifth Embodiment

Figure 9:
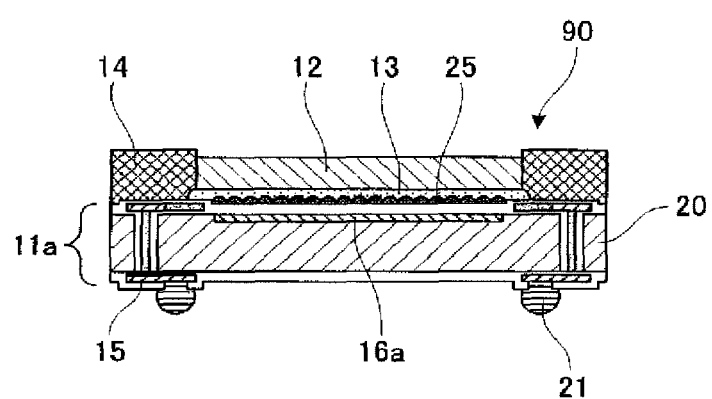
FIG. 9 is a sectional view showing an optical device according to a fifth embodiment.

Next, an optical device according to the fifth embodiment of the present invention will be described. FIG. 9 is a sectional view showing the optical device according to the fifth embodiment. Here, as an example of the optical device, a solid-state image device 90 will be described.

The solid-state image device 90 is equipped with a solid-state image element 11a, a transparent member 12 adhered on an imaging region 16a of the solid-state image element 11a using a light-transmitting adhesive 13, and a light shielding molding resin 14 that coats the side surfaces of the transparent member 12 and the major surface of the solid-state image element 11a excluding the region coated by the transparent member 12. The thickness of the molding resin 14 is larger than the thickness of the transparent member 12 by a range of 20 µm to 150 µm, preferably a range of 50 µm to 100 µm. Thereby, the upper surface of the molding resin 14 is formed to be higher than the upper surface of the transparent member 12.

The operation of the above-described configuration will be described. Since the upper end portion of the molding resin 14 is projected from the upper surface of the transparent member 12, the lowering of mechanical strength due to the thickness reduction of a semiconductor substrate 20 can be prevented by the thickened molding resin 14. Flares and smears caused by stray light generated by the invasion of external reflected light from the side surfaces of the transparent member 12 can also be prevented. Furthermore, since the solid-state image device 90 does not require housing, and the transparent member 12 is directly adhered on the major surface of the solid-state image element 11a, the reduction of the size and thickness of chips can be realized. Since the side surfaces of the transparent member 12 are completely coated with the molding resin 14, a solid-state image device 90 that excels in optical properties can be realized.

Next, a method for manufacturing the solid-state image device 90 will be described referring to FIGS. 10A to 10D. FIGS. 10A to 10D show sectional views illustrating the step of resin molding of the solid-state image element 11a, the step of making individual solid-state image devices 90, and the step of peeling off a surface protective seal 91 in the method. Since the step of preparing a solid-state image element wafer 40 formed of a plurality of the solid-state image elements 11a vertically and horizontally arranged at even intervals, and the step of forming conductive electrodes 21 on electrodes for external connection 15 are the same as those in the first embodiment shown in FIG. 4A and FIG. 5C, respectively, the detailed description thereof will be omitted here.

Figure 10A:
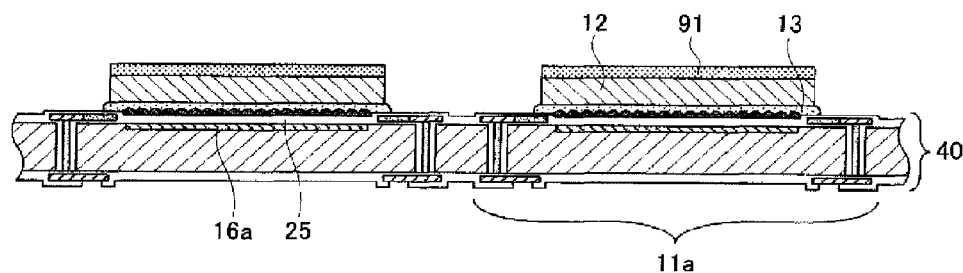
FIG. 10A is a step sectional view showing the step of adhering a transparent member in a method for manufacturing the optical device according to the fifth embodiment.

FIG. 10A is a step sectional view showing the step of adhering the transparent member in the method for manufacturing the optical device according to the fifth embodiment, and is a sectional view showing the step of adhering the transparent member 12 on the imaging region 16a of each solid-state image element 11a. Transparent members 12 made of borosilicate glass are placed on the imaging region 16a of each solid-state image element 11a to which the light-transmitting adhesive 13 is applied of the solid-state image element wafer 40 so as not to introduce the air. The transparent member 12 has a size to coat the entire surface of the imaging region 16a, and the surface protective seal 91 has previously been adhered on the upper surface of the transparent member 12 (major surface opposite to the solid-state image element 11a). Thereby, the adhesion of dust on the upper surface of the transparent member 12 can be avoided. The transparent member 12 may also be placed on the light-transmitting adhesive 13 while defoaming in a reduced-pressure atmosphere.

Then, the transparent member 12 is aligned in parallel with the surface of the imaging region 16a at the proper location of the imaging region 16a, and ultraviolet beams having a predetermined optical energy are radiated so as to cure the light-transmitting adhesive 13 to adhere the transparent member 12 on the micro lenses 25 of the imaging region 16a. Alternatively, the transparent member 12 may be adhered by heating after the irradiation of ultraviolet beams. The transparent member 12 may be made of any of quartz, calcite, alumina, and a transparent resin.

Figure 10B:
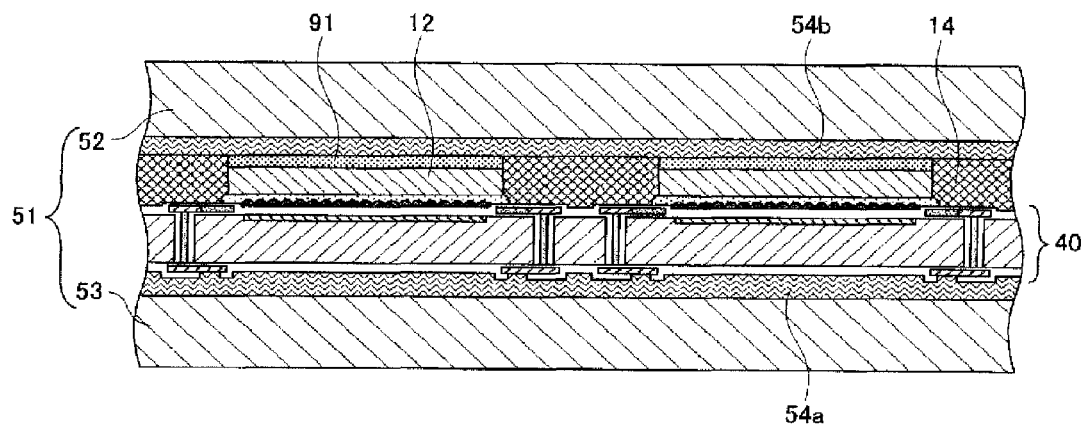
FIG. 10B is a step sectional view showing the resin molding step in the method for manufacturing the optical device according to the fifth embodiment.

FIG. 10B is a step sectional view showing the resin molding step in the method for manufacturing the optical device according to the fifth embodiment. Since this step can be carried out by transfer molding using a mold 51 as in the first embodiment shown in FIG. 5A, the detailed description will be omitted. In this step, however, since the surface protective seal 91 is adhered on the surface of the transparent member 12, when an upper mold 52 and a lower mold 53 of the mold 51 are clamped, the surface protective seal 91 is compressed to a release sheet 54b on the upper mold 52.

Figure 10C:
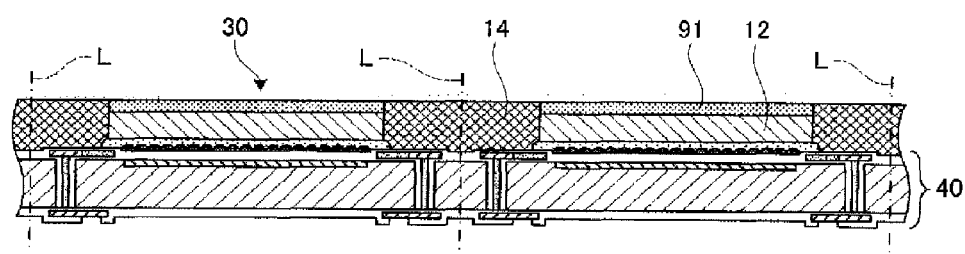
FIG. 10C is a step sectional view showing the step of fabricating an optical device wafer in the method for manufacturing the optical device according to the fifth embodiment.

Then, the mold for resin molding 51 is opened after a predetermined length of time, and as shown in FIG. 10C, which is a step sectional view showing the step of fabricating the optical device wafer in the method for manufacturing the optical device according to the fifth embodiment, the resin-molded solid-state image element wafer 40, that is a solid-state image device wafer 30 (an example of optical device wafers), is taken out. At this time, the upper surface of the surface protective seal 91 is formed to be substantially flush (the same height) with the upper surface of the molding resin 14. Thereafter, the solid-state image device wafer 30 is cut along the dividing line L with a dicer into individual solid-state image devices 90. At this time, since the surface of the transparent member 12 is coated with the surface protective seal 91, the transparent member 12 is not damaged in the dicing step.

Figure 10D:
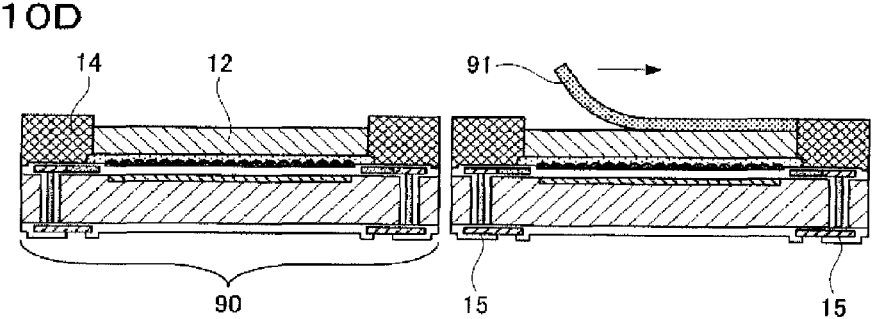
FIG. 10D is a step sectional view showing the step of removing a surface protective seal in the method for manufacturing the optical device according to the fifth embodiment.

FIG. 10D is a step sectional view showing the step of removing the surface protective seal in the method for manufacturing the optical device according to the fifth embodiment, and is the step of peeling off the surface protective seal 91 on the transparent member 12. In this step, the surface protective seal 91 is peeled off and removed from the transparent member 12, and the upper surface of the clean transparent member 12 is exposed. Thereby, since the upper surface of the molding resin 14 is formed to be higher than the upper surface of the transparent member 12, the strength is improved, and since the side surfaces of the transparent member 12 are completely coated with the molding resin 14, flares and smears can be prevented, and a solid-state image device 90 that excels in optical properties can be realized.

Thereafter, the conductive electrodes 21 are joined to the electrodes for external connection 15 of each solid-state image device 90. Since the configuration for applying the solid-state image device 90 obtained in the fifth embodiment to digital cameras or endoscopes for disaster, for investigating buried cultural properties and for medical treatments to fabricate electronic devices is the same as in the electronic devices described in the third and fourth embodiments, the description thereof will be omitted here.

Sixth Embodiment

Figure 11:
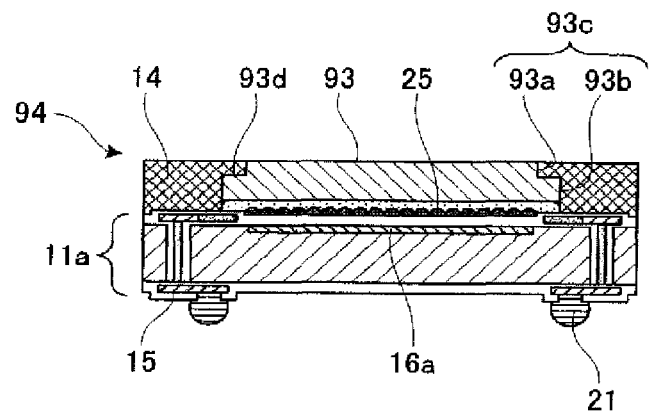
FIG. 11 is a sectional view showing an optical device according to a sixth embodiment.

FIG. 11 is a sectional view showing an optical device according to the sixth embodiment. The same elements as in FIG. 2 of the above-described first embodiment are denoted by the same reference numerals and characters, and the description thereof will be omitted here.

A transparent member 93 has a size to coat the entire surface of an imaging region 16a on which micro lenses 25 of a solid-state image element 11a are formed, and both upper and lower surfaces of the transparent member are processed to be optically flat and are parallel to each other.

A side surface of the transparent member 93 has a step 93c consisting of an upper step 93a and a lower step 93b. The projection plane of the lower step 93b is rectangular and larger than the imaging region 16a of the solid-state image element 11a both in length and width, and larger than the projection plane of the upper step 93a. The projection plane of the upper step 93a is rectangular and has the substantially same size as the imaging region 16a of the solid-state image element 11a. A step plane 93d of the upper step 93a and the lower step 93b is formed above half the thickness of the transparent member 93.

The edges of the upper step 93a may be chamfered. In the projection plane of the lower step 93b, four corners may be cut at about 45°, and in addition, the edges of one of or both upper and lower surfaces may be chamfered. Although the material of the transparent member 93 is a borosilicate glass plate, a low-pass filter formed of either quartz or calcite may be used, and a transparent epoxy resin, acrylic resin, or transparent alumina may also be used. The thickness and transmissivity of the transparent member 93 are the same as in the first embodiment.

The operation of the above-described configuration will be described.

In a solid-state image device 94, since a layer of a molding resin 14 coats the side surface of the upper step 93a, the side surface of the lower step 93b and the step plane 93d of the transparent member 93, and the projection plane of the upper step 93a has the substantially same size as the imaging region 16a of the solid-state image element 11a, the same effect as when a light-shielding plate is disposed on the transparent member 93 can be obtained in addition to the advantage obtained in the first embodiment. Furthermore, the adhesion area of the transparent member 93 and the molding resin 14 is enlarged, the delamination of the transparent member 93 from the molding resin 14 can be prevented, and the invasion of moisture from the boundary between the transparent member 93 and the molding resin 14 can also be prevented.

Seventh Embodiment

Figure 12:
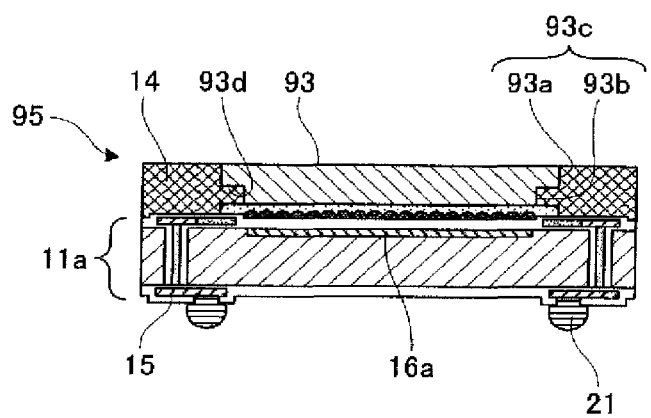
FIG. 12 is a sectional view showing an optical device according to a seventh embodiment.

FIG. 12 is a sectional view showing an optical device according to the seventh embodiment, and specifically, a sectional view showing a solid-state image device 95 according to the seventh embodiment, which is a modification of the sixth embodiment. The projected plane of a lower step 93b of a transparent member 93 has a rectangular shape of the substantially same size as an imaging region 16a, and is smaller than the projected plane of an upper stage 93a.

Thereby, similarly to the sixth embodiment, in addition to the advantage obtained in the first embodiment, the same effect as when a light-shielding plate is disposed on the transparent member 93 can be obtained, and since the adhesion area of the transparent member 93 and a molding resin 14 is enlarged, the delamination of the transparent member 93 from the molding resin 14 can be prevented, and the invasion of moisture from the boundary between the transparent member 93 and the molding resin 14 can also be prevented in addition to the advantage obtained in the first embodiment.

Eighth Embodiment

Figure 13:
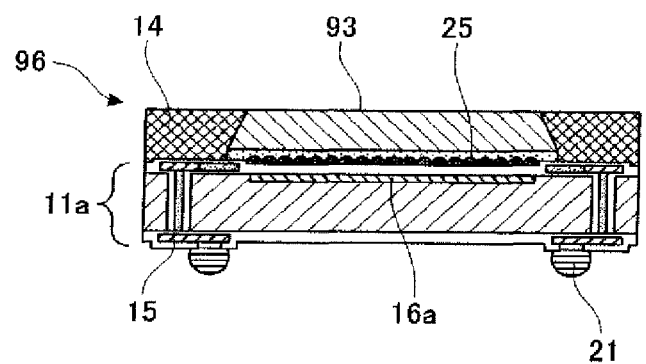
FIG. 13 is a sectional view showing an optical device according to an eighth embodiment.

In the solid-state image devices according to the sixth and seventh embodiments, although the step 93c is formed on the side surface of the transparent member 93, as a solid-state image device 96 according to the eighth embodiment, the side surfaces of the transparent member 93 may be tilted as shown in a sectional view of an optical device according to the eighth embodiment in FIG. 13. Thereby, since the adhesion area of the transparent member 93 and a molding resin 14 is enlarged, the delamination of the transparent member 93 from the molding resin 14 can be prevented.

Since the methods for manufacturing the solid-state image devices 94 to 96 of the sixth to eighth embodiments, and the incorporation to the set are the same as in the first to fifth embodiments, the description thereof will be omitted.

By achieving the configurations, manufacturing methods, and assembly to the electronic devices of each solid-state image device in the above-described embodiments, inexpensive, small and thin solid-state image devices and electronic devices that excel in optical properties can be provided. Although in the sixth to eighth embodiments the solid-state image devices are described, it is needless to say that the similar configuration can also be applied to light-receiving elements, such as photo ICs and photo couplers.

Ninth Embodiment

Figure 14A:
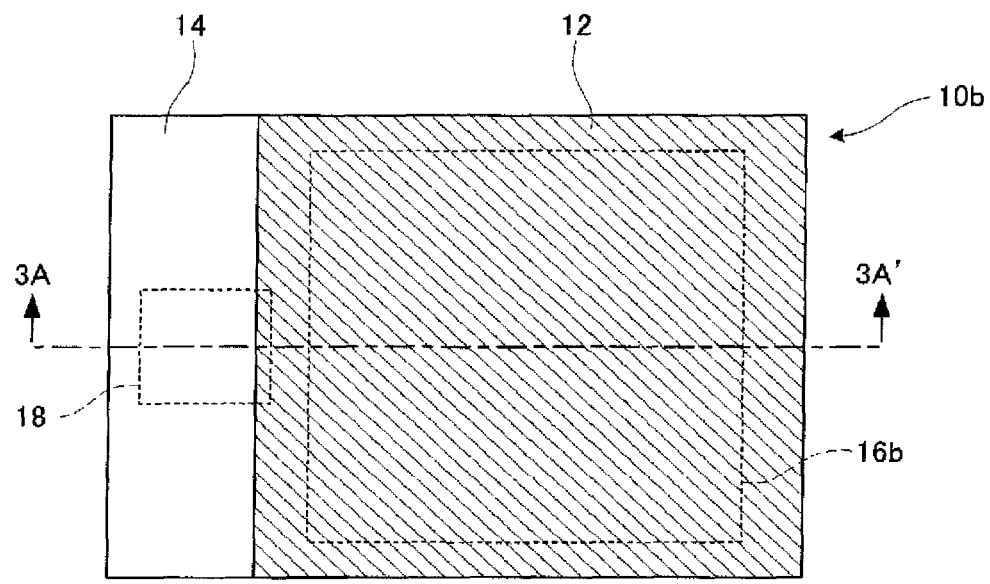
FIG. 14A is a plan view showing the configuration of an optical device according to a ninth embodiment viewed from the transparent member side.
Figure 14B:
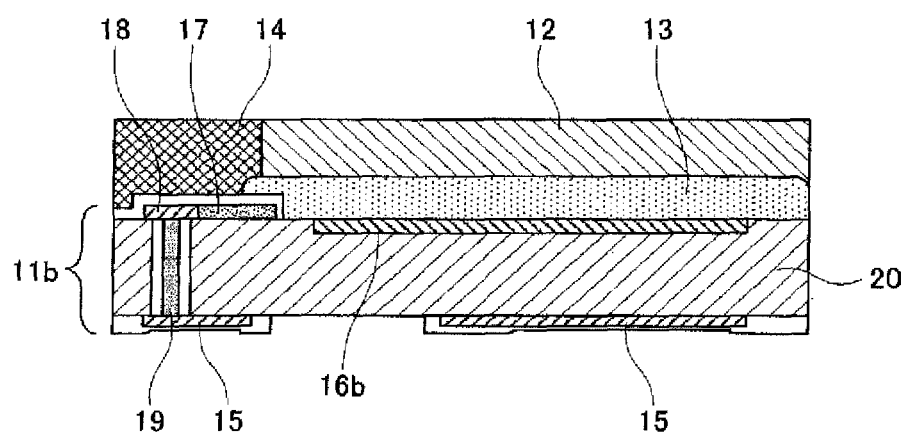
FIG. 14B is a sectional view showing the configuration of the optical device according to the ninth embodiment.
Figure 15A:
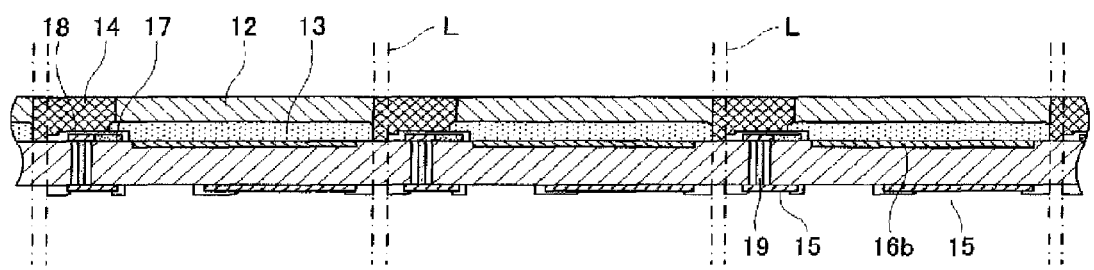
FIG. 15A is a sectional view showing the configuration of the optical device wafer according to the ninth embodiment.
Figure 15B:
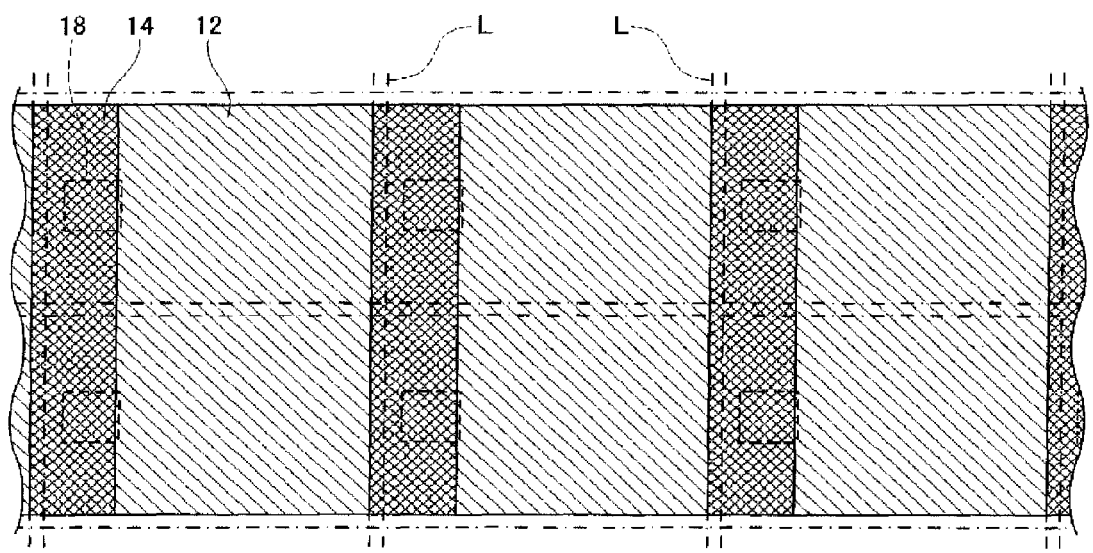
FIG. 15B is a plan view showing the configuration of the optical device wafer according to the ninth embodiment.
Figure 16:
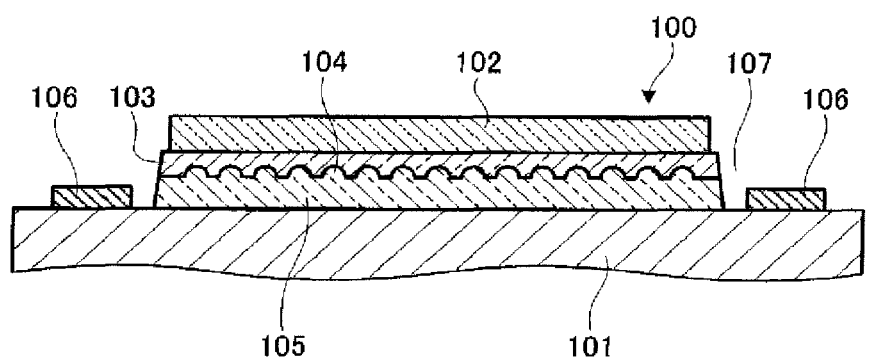
FIG. 16 is a sectional view showing a conventional solid-state image device.
Figure 17A:
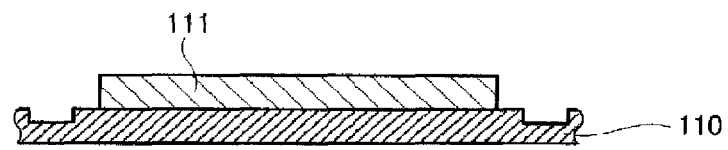
FIGS. 17A to 17G are step sectional views showing a method for manufacturing the conventional solid-state image device.
Figure 17B:
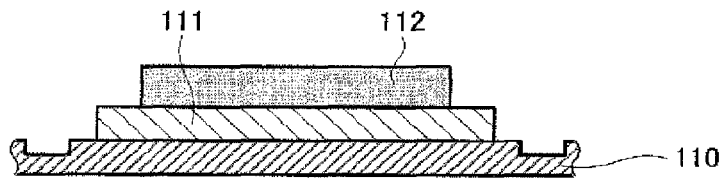
Figure 17C:
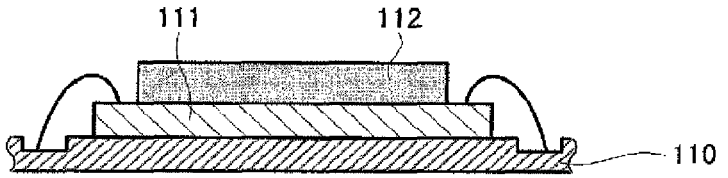
Figure 17D:
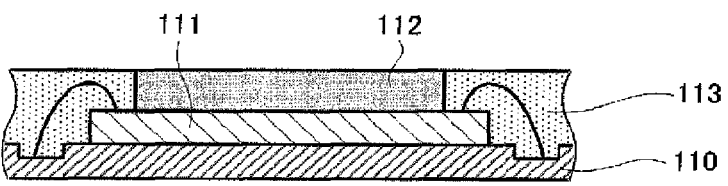
Figure 17E:
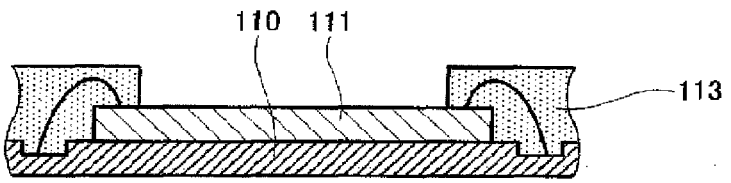
Figure 17F:
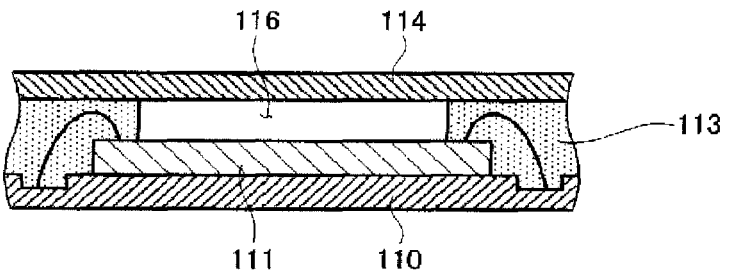
Figure 17G:
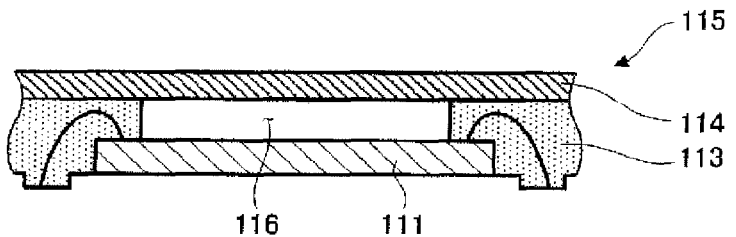

FIG. 14A is a plan view showing the configuration of an optical device according to the ninth embodiment viewed from a transparent member side; and FIG. 14B is a sectional view showing the configuration of the optical device according to the ninth embodiment, and is a sectional view taken along the line 3A-3A'. FIG. 15A is a sectional view showing the configuration of an optical device wafer according to the ninth embodiment; and FIG. 15B is a plan view showing the configuration of the optical device wafer according to the ninth embodiment.

In the ninth embodiment, the configuration of an LED device 10b will be described using a light emitting element, particularly an LED (light emitting diode) device 10b as an example of optical devices referring to FIGS. 14A, 14B, 15A and 15B. The ninth embodiment can also be applied to a similar light emitting element, such as a surface emitting laser.

The LED device 10b is equipped with an LED element 11b being an example of optical elements, a transparent member 12, and a molding resin 14. A light emitting region 16b is formed on the major surface of the LED element 11b and an element electrode 18 is provided around the light emitting region 16b. The element electrode 18 is electrically connected to the light emitting region 16b, and on the back surface opposite to the major surface of the LED element 11b, a plurality of electrodes for external connection 15 are provided. In the case of the LED element 11b, these electrodes for external connection 15 are normally composed of two terminals: one is conducted from the element electrode 18 to the lower surface through a penetration electrode 19, and the other is directly connected to the back surface of the LED element 11b to constitute the electrode for external connection 15.

As the materials for a semiconductor substrate 20, group III-V compounds and group II-VI compounds are mainly used on a semiconductor laser and LED (light emitting diode) and in the case of the light emitting diode, GaN substrate and the like are often used.

The transparent member 12 is adhered on the major surface of the LED element 11b using a light-transmitting adhesive, such as a light-transmitting adhesive 13, and is disposed so as to coat the entire surface of the light emitting region 16b. The end surface of the transparent member 12 has no molding resin provided on three of four sides, and the transparent member 12 is exposed on the end surface.

Such a form can be produced if the transparent member 12 is made to be reed-shaped in the manufacturing step, because a plurality of the LED elements 11b can be easily fabricated in the wafer or block state. Although a glass plate can be used as the material for the transparent member 12, when the step of dividing the LED device 10b is considered, for example, an organic transparent substrate, such as a transparent acrylic resin, a transparent silicone resin, and a transparent epoxy resin should be used for ease of dicing.

When an organic transparent substrate, such as a transparent acrylic resin, a transparent silicone resin, and a transparent epoxy resin is used, the thickness of the transparent member 12 is within a range of 10 μm to 100 μm, preferably of 20 μm to 80 μm. The reason why the minimum thickness is 10 μm is that the size and thickness reduction is realized so that the mounting height of the LED (light emitting diode) device composed of the transparent member 12, the light-transmitting adhesive 13, the molding resin 14, the LED element 11b and the electrode for external connection 15 when mounted is 100 μm or less; and the reason why the maximum thickness is 100 μm is that the size and thickness reduction to 300 μm or less is realized.

The reason why the preferable range is from 20 μm to 80 μm is that this range of thickness is the thickness enabling the LED (light emitting diode) device 10b to be most stably produced using the existing manufacturing technology, and for realizing an inexpensive, small and thin LED (light emitting diode) device 10b by applying inexpensive general-purpose materials as the components. When a transparent resin is used for the transparent member 12, the thickness must be determined considering the transmission efficiency of each transparent member 12.

The light-transmitting adhesive 13 is an optically light-transmitting adhesive used when the transparent member 12 is fixed on the light emitting region 16b, and can be, for example, acrylic resins, epoxy resins compounded so as to have no absorption end within the wavelength range of visible light, or polyimide resins. The light-transmitting adhesive 13 can be cured by ultraviolet irradiation, heating, or the combination thereof, and the cured light-transmitting adhesive 13 has a low refraction index.

The molding resin 14 particularly coats the element electrode 18 on the major surface of the LED element 11b, and is a resin formed to have a flat upper surface, and the thickness of the molding resin 14 is substantially the same as the total thickness of the transparent member 12 and the light-transmitting adhesive 13. In the case of the light emitting element, considerations for light-shielding properties are not required, and it is only necessary to firmly protect the element electrode 18 from moisture and mechanical stress. Although an epoxy resin is mainly used as the material for the molding resin 14, when a low-elasticity cured article is used for improving resistance to thermal shock and moisture, biphenyl resins or silicone resins may also be used.

Although not shown in the drawing, in place of the molding resin 14, the transparent member 12 and the light-transmitting adhesive 13 may be adhered on the entire major surface of the LED element 11b. In this case, the total thickness of the transparent member 12 and the light-transmitting adhesive 13 must combine the light emitting properties of the LED (light emitting diode) device 10b, and the properties of moisture resistance, heat resistance and the like.

As described above, with the configuration in which the light emitting region 16b is protected with the transparent member 12 and the element electrode 18 is protected with the molding resin 14, the mechanical damage on the major surface of the LED (light emitting diode) device 10b can be prevented. Also since the entire major surface of the LED (light emitting diode) device 10b is coated with the molding resin 14 and the light-transmitting adhesive 13, the strength lowering of the LED (light emitting diode) device 10b can be prevented.

Since the LED (light emitting diode) device 10b does not require as high reliability as the above-described solid-state image device 10a, it is not so required to firmly prevent the invasion of moisture from the adhesion boundary between the transparent member 12 and the LED element 11b compared with the solid-state image device 10a. The reason for this is that although moisture resistance is important for the solid-state image device 10a because micro lenses 25 are disposed on the imaging region 16a, the LED (light emitting diode) device 10b does not require micro lenses. Furthermore, the number of electrodes for external connection 15 is much smaller compared with the solid-state image device 10a. Normally, the solid-state image device 10a has several to several tens of pins. However, an LED (light emitting diode) or a surface emitting laser generally has two pins, or three pins including a pin for a grounding electrode and the like. Although the size of the solid-state image device 10a is a maximum about 10 mm×10 mm, the size of the LED (light emitting diode) device 10b is about 0.1 mm×0.1 mm to 1.0 mm×1.0 mm. Therefore, even if the end surface of the transparent member 12 has no molding resin and is exposed, the LED (light emitting diode) device 10b is sufficient for practical use.

If the end surface of the transparent member 12 is exposed, the transparent member 12 can be made to be reed-shaped in the manufacturing step, the LED elements 11b can be fabricated at lower costs.

Next, FIGS. 15A and 15B show diagrams illustrating the state in which a plurality of the LED (light emitting diode) devices 10b are vertically and horizontally arranged; FIG. 15A is a sectional view, and FIG. 15B is a plan view viewed from the transparent member 12 side in FIG. 15A.

The state is constituted by the plurality of LED (light emitting diode) devices 10b, the transparent members 12 disposed on the LED elements 11b, the light-transmitting adhesive 13 for adhering the LED elements 11b to the transparent members 12, and the molding resin 14 for molding the element electrodes 18.

A wafer or block on which the plurality of LED (light emitting diode) devices 10b are formed is divided along the dividing lines L, and only accepted products are transferred to the next step. The LED (light emitting diode) devices 10b rejected at the electrical or optical test are discarded. For dividing, the wafer or block is cut using a dicing blade fabricated by solidifying diamond abrasive grains with a bonding material at a high-speed rotation (1,000 to 30,000 rpm). Alternatively, a method for dividing using a laser may also be used. When the transparent members 12 are made of glass plates, since cracks are easily produced, if the thickness portions of the transparent members 12 are cut using the laser, and the thickness portions of the LED elements 11b are cut using the dicing blade, a high-quality LED (light emitting diode) device 10b without end surface cracking can be obtained.

When the dicing blade is used for dividing, the suitable mounting height of the LED (light emitting diode) device 10b is not less than 100 μm. When the laser is used for dividing, the suitable mounting height of the LED (light emitting diode) device 10b is less than 100 μm. Particularly when the laser is used, the most suitable mounting height is less than 50 μm. The reason for this is that if the mounting height is less than 50 μm, for example, if the total thickness of the LED (light emitting diode) device 10b is 30 μm, it is not required to repeat the radiation of laser beams multiple times, and the wafer can be divided by one radiation.

What is claimed is:

1. An optical device comprising:
   a package including an optical element and a light-transmitting member disposed over the optical element, the light-transmitting member having a first side surface and a second side surface opposite to the first side surface,
   wherein the package has a third side surface facing the first side surface of the light-transmitting member and a fourth side surface facing the second side surface of the light-transmitting member,
   a distance between the first side surface of the light-transmitting member and the third side surface of the package is longer than a distance between the second side surface of the light-transmitting member and the fourth side surface of the package.

2. The optical device according to claim 1, wherein the second side surface of the light-transmitting member and the fourth side surface of the package lie in a same plane.

3. The optical device according to claim 1, wherein the optical element has an optical region, and a distance between the third side surface of the package and the optical region is longer than a distance between the fourth side surface of the package and the optical region.

4. The optical device according to claim 1, further comprising a resin between the first side surface of the light-transmitting member and the third side surface of the package.

5. The optical device according to claim 4, wherein a side surface of the resin and a side surface of the optical element lie in a same plane.

6. The optical device according to claim 4, wherein a side surface of the resin and a side surface of the optical element are aligned in a same vertical plane.

7. The optical device according to claim 1, wherein a side surface of the optical element and the second side surface of the light-transmitting member lie in a same plane.

8. The optical device according to claim 1, wherein all portions of the package disposed on the third side surface of the package lie in a same plane.

9. The optical device according to claim 1, wherein all portions disposed on the fourth side surface of the package lie in a same plane.

10. The optical device according to claim 1, further comprising a first conductive portion and a second conductive portion disposed under the optical element,
wherein the optical element has an optical region,
the first conductive portion is disposed vertically under the optical region,
the second conductive portion is disposed at a region except for a region vertically under the optical region, and
a width of the first conductive portion is larger than a width of the second conductive portion.

11. The optical device according to claim 10, wherein the first conductive portion is an electrode for external connection.

12. The optical device according to claim 10, wherein the second conductive portion is an electrode for external connection.

13. The optical device according to claim 10, wherein the first conductive portion and the second conductive portion are attached to a lower surface of the optical element.

14. The optical device according to claim 1, wherein the optical element has an optical region, and the optical region has a light emitting region.

15. The optical device according to claim 1, further comprising an electrode for external connection disposed under the optical element,
wherein the optical element has an optical region,
the electrode for external connection is disposed at a region except for a region vertically under the optical region.

16. The optical device according to claim 1, wherein the second side surface of the light-transmitting member and the fourth side surface of the package are aligned in a same vertical plane.

17. The optical device according to claim 1, further comprising a first conductive portion and a second conductive portion disposed under the optical element,
wherein the optical element includes an optical region,
the first conductive portion is disposed under the optical region within a horizontal plane defined by a surface area of the optical region,
the first conductive portion is wider than the second conductive portion.

18. The optical device according to claim 1, further comprising an electrode for external connection disposed under the optical element,
wherein the optical element has an optical region,
the electrode for external connection is disposed outside of a horizontal plane defined by a surface area of the optical region.

* * * * *